United States Patent [19]
Conte et al.

[11] Patent Number: 5,487,901
[45] Date of Patent: Jan. 30, 1996

[54] PROCESS FOR PREPARING PHARMACEUTICAL TABLET CAPABLE OF RELEASING THE ACTIVE INGREDIENTS CONTAINED THEREIN AT SUBSEQUENT TIMES

[75] Inventors: Ubaldo Conte, Busto Arisizio; Aldo La Manna; Lauretta Maggi, both of Pavia, all of Italy

[73] Assignee: Ekita Investments N.V., Curacao, Netherlands Antilles

[21] Appl. No.: 248,338

[22] Filed: May 24, 1994

[30] Foreign Application Priority Data

May 31, 1993 [IT] Italy .................... MI93A1120

[51] Int. Cl.[6] ........................... A61K 9/22
[52] U.S. Cl. ................ 424/472; 424/464; 424/474; 424/475
[58] Field of Search ................... 424/472, 474, 424/475, 464

[56] References Cited

FOREIGN PATENT DOCUMENTS

| 0230654 | 8/1987 | European Pat. Off. . |
| 0274734 | 7/1988 | European Pat. Off. . |
| 20100858 | 3/1972 | France . |

*Primary Examiner*—D. Gabrielle Phelan

[57] ABSTRACT

A pharmaceutical tablet capable of releasing the active ingredients contained therein at subsequent times produced via the steps of: a) preparing a tablet consisting of three superposed layers, the upper layer containing an active ingredient, the intermediate layer not containing any active ingredient and forming a barrier-type layer, and the lower layer containing an active ingredient, said upper layer presenting a raised top, b) coating the tablet entirely with an impermeable polymeric film, and c) removing said raised top and thus allowing contact of the abraded upper layer surface with the environment.

10 Claims, 1 Drawing Sheet

PROCESS FOR PREPARING PHARMACEUTICAL TABLET CAPABLE OF RELEASING THE ACTIVE INGREDIENTS CONTAINED THEREIN AT SUBSEQUENT TIMES

PRIOR ART

The problem of optimizing the release of drugs from matrices to specific site and/or at a programmed rate is of consequence to several fields of application, both in agriculture (e.g. use of fertilizers and/or herbicides and/or selective pesticides) and in human and animal therapy.

In the aforesaid fields, very many are the research efforts made to develop systems that utilize release of an active agent at a constant rate, independently of- the medium where the drug-containing matrix or system is placed.

In the biomedical field, with special regard to humans, in vitro systems capable of releasing a drug at a constant rate and over a scheduled period of time were extensively studied also with a view to gaining information on a prospective identical or analogous behaviour in vivo.

Said systems are targeted for an in-vivo drug release according to zero-order kinetics, which allows maintaining a constant plasmatic level of the drug.

Among said innovative pharmaceutical forms for oral administration, mention may be made of the therapeutic systems denominated osmotic pumps, usually known as OROS systems, as are disclosed in U.S. Pat. No. 4,160,020 (1979).

The aforesaid embodiments have the undoubted advantage of allowing a drastic simplification of the posologic schemes, which in many cases envisage a single daily administration and, consequently, result in a better patient's compliance therewith.

The advantages of constant release pharmaceuticals are, however, evident only when the drug plasmatic levels are within a precise range for a long time: below said range the drug is inactive; above it, untoward manifestations and side effects and/or toxic—even extremely dangerous—phenomema may occur.

Furthermore, in some pathological conditions and in some diseases whose morbid manifestations are connected with circadian rhythms, it would be advisable to administer pharmaceuticals capable of releasing the active ingredient in sequential pulses to prevent the onset of an exacerbated painful or morbid manifestation connected with said circadian rhythms.

Said type of administration may be required, e.g., to treat rheumatic symptomatology and/or insomnia.

As concerns rheumatic disease, it is known that the onset of exacerbated pain in joints very frequently occurs 4 to 5 hours after the beginning of sleep (that is, usually, in the dead of night) and, therefore, a further drug administration is sometimes required.

An analogous behaviour is shown by patients suffering from insomnia. Said condition is often treated with drugs (e.g. benzodiazepines) producing a very fast action (beginning of sleep), but having a short-lasting effect (4 to 5 hours).

In said and in analogous conditions, there is an evident need for pharmaceuticals and/or therapeutic systems capable of releasing one or various active ingredient/s in pulses.

A classic example of pulsing release is given by the simultaneous administration of an immediate release tablet and an enteric coated tablet, which dispenses the active ingredient in the intestine, said administration being made possible by packing said tablets into a single pharmaceutical form (e.g. a capsule). In that case, however, the release of the second dose of drug will be closely related to the gastric emptying time which, as known, depends of several factors, such as the composition and amount of food eaten.

A further achievement in the sector of pulsing release is disclosed in Italian patent application No. 19064/A87, which claims the preparation of a three-layer tablet, wherein two layers are coated with an envelope consisting of an impermeable polymeric material insoluble in water or soluble in an alkaline medium.

The description and examples conveyed therein set forth the preparation of a three-layer tablet, the first and third layers thereof containing the active ingredient, and the intermediate layer, placed between the first and third layers, consisting of a gelable polymeric material.

Said tablet which is characterized, as already mentioned, by an envelope coating the second and third layers thereof, can release a dose of drug immediately and a second dose after 30 min approx. However, there is a dramatic limitation on the production of said tablet: the tablet partial coating is handmade, time consuming, hardly standardizable, and, in any case, cannot be exploited on a commercial scale.

SUMMARY

The pharmaceutical tablet as per the present invention, capable of releasing the drugs at subsequent times, comprises three superposed layers, i.e.:

- an upper layer containing an active ingredient, suitably formulated so as to allow an immediate drug release;
- an intermediate layer not containing any drug, which is formulated so as to slowly interact with the dissolution medium, serving the function of providing a barrier to the drug release from the layer underneath;
- a lower layer of the same formulation as the upper layer, containing an identical or a different active ingredient, and characterized by being entirely coated—with the only exception of a small area of the upper side—with an impermeable polymeric film, consisting of a polymer either insoluble or exhibiting a delayed solubility or a solubility depending on the pH of the medium.

Said tablet is produced on the basis of a procedure characterized by the steps of a) preparing a tablet consisting of the three layers as defined above, wherein the upper side of the upper layer has a raised top above said upper surface;

b) coating the tablet as per step a) entirely with an impermeable polymeric film;

c) removing said raised top and thus allowing contact of the abraded upper layer surface with the environment.

DETAILED DESCRIPTION OF THE INVENTION

The pharmaceutical tablet of the present invention, which is capable of releasing the drugs at subsequent times, consists of three layers in stacked relation, i.e.:

- an upper layer containing an active ingredient and suitable excipients;
- an intermediate layer not containing any drug, which is formulated so as to form a barrier-type layer;

a lower layer of the same composition as the upper layer, containing an identical or a different active ingredient.

Said tablet is characterized by being entirely coated—with the only exception of a small area of the upper side—with an impermeable polymeric film, either insoluble or exhibiting a delayed solubility or a solubility depending on the pH of the medium.

Said tablet is produced on the basis of a procedure consisting of the steps of a) preparing a tablet consisting of the three layers as defined above, wherein the upper side of the upper layer has a raised portion with respect to the remaining surface of the same side;

b) coating the tablet as per step a) entirely with an impermeable polymeric film as defined above;

c) removing said raised portion to allow contact of the correspondent upper layer surface with environment.

The characteristics of the tablets of the present invention and the procedure for the preparation of same will now be described in greater detail, with reference to certain exemplary embodiments as also illustrated in the drawings, to which the present invention is not intended to be confined.

In the figures, 1 indicates the tablet upper layer, 2 the intermediate layer, 3 the lower layer, 4 the coating, 5 the spherical top, 6 the area of the upper layer wherefrom the spherical raised top has been removed, and 7 the area of the upper layer wherefrom the ring-shaped raised top has been removed.

Figure 3:
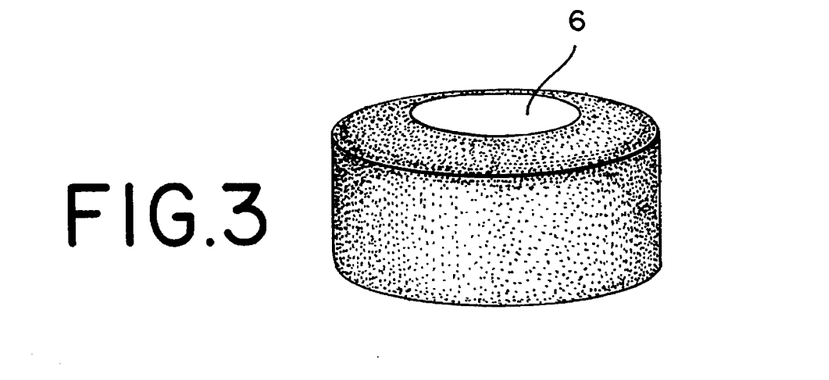
FIG. 3 is an axonometric projection of the tablet of FIG. 1 after removal of the raised top.
Figure 4:
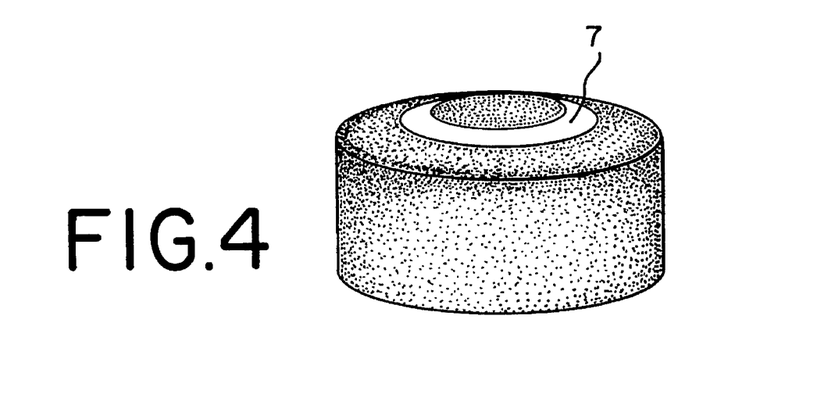
FIG. 4 is an axonometric projection of a tablet after removal of a ring-shaped raised top.

On coming into contact with water or intestinal fluids, areas 6 and 7—being uncoated—allow a fast release of the active ingredient contained in layer 1.

The claimed tablets may be easily produced by automated industrial procedures.

Figure 1:
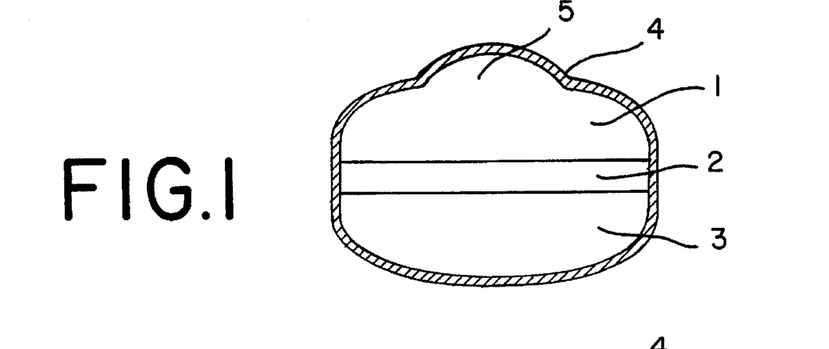
FIG. 1 is a side elevation view of a tablet with a spherical raised top.

Tablets as per FIG. 1 are produced by a three compressed layers and entire tablet coating technique.

Tablets are then fed to a hopper provided with a vibrating system suitably adjusted so as to allow an identical positioning of all tablets, i.e. the raised top upwards.

Tablets are then distributed on a suitable belt or conveying system and caused to pass under a precision milling machine or another appropriate abrading system which scrapes out the raised top and, therefore, removes the coating from the area involved in the abrasion process.

Therefore, in the tablet so obtained (FIG. 2), a portion of the upper side may immediately come into contact with aqueous fluids and fast release the active ingredient contained in the upper layer; instead, the rest of the tablet (i.e. the intermediate and lower layers) is uniformly coated with said impermeable film.

The formulation of said fast-releasing upper layer comprises, in addition to the active ingredient, excipients favouring layer disintegration and, therefore, facilitating a fast release of the drug contained in said layer.

Said excipients are selected from the group consisting of cross-linked polyvinylpyrrolidone, low- and medium-molecular-weight hydroxypropyl cellulose and hydroxypropyl methylcellulose, cross-linked sodium carboxymethylcellulose, carboxymethyl starch, potassium methacrylate-divinylbenzene copolymer, polyvinyl alcohols, starches, starch derivatives, microcrystalline cellulose and cellulose derivatives, β-cyclodextrin and dextrin derivatives, mannitol, lactose, sorbitol, and xylitol.

The amount of said active ingredient, in respect of the layer total weight, is 1.0 to 90% by wt. and the amount of said excipients, always in respect of the layer total weight, is 1.0 to 90% by wt. and preferably 20 to 70% by wt.

Other adjuvants may be used, i.e. the so-called effervescent substances, which are capable of bringing about a rapid layer disintegration, once it comes into contact with aqueous fluids and, preferably, with gastric juice. Said adjuvants may be selected among carbonates and bicarbonates of sodium and of other alkali metals or alkaline earth metals, glycocoll sodium carbonate and other pharmaceutically acceptable salts having the property of effervescing in an acid medium. Depending on the pH of the medium where a rapid layer disintegration has to take place, the formulation may include other substances, such as citric acid or tartaric acid or fumaric acid, which cause effervescence and a rapid layer disintegration.

Other substances currently used in the typical pharmaceutical practice can be used, such as diluents, buffers, adsorbents, etc., and in particular starch, pregelled starch, calcium phosphate, mannitol, lactose, saccharose, glucose, sorbitol, microcrystalline cellulose, and binding agents, such as gelatin, polyvinylpyrrolidone, methylcellulose, starch solution, ethylcellulose, arabic gum, tragacanth gum.

Other excipients can be used, such as for example magnesium stearate, stearic acid, colloidal silica, glyceryl monostearate, polyoxyethylene glycols with molecular weights in the range 400 to 50,000, hydrogenated castor oil, waxes, and mono-, di-, and trisubstituted glycerides.

Said upper layer is 0.5 to 5 mm thick.

The composition of the intermediate or barrier-type layer, i.e. of the element controlling the time taken by the drug to be released from the lower layer, comprises gelable and/or soluble and/or erodible polymeric substances as-well as adjuvants and plasticizers. Said polymeric substances of said layer are selected from the group consisting of hydroxypropyl methylcellulose with molecular weight in the range 1,000 to 4,000,000, hydroxypropyl cellulose with molecular weight in the range 2,000 to 2,000,000, carboxyvinyl polymers, polyvinyl alcohols, glucans, scleroglucans, mannans, xantan gums, alginic acid and derivatives thereof, poly(methyl vinyl ethers/maleic anhydride), carboxymethylcellulose and derivatives thereof, ethylcellulose, methylcellulose, and cellulose derivatives in general.

The amount of said polymeric substances, in respect of the layer total weight, is 5 to 90% by wt. and preferably 50 to 90% by wt. Adjuvants are selected from the group consisting of glyceryl monostearate and semisynthetic triglyceride derivatives, semisynthetic glycerides, hydrogenated castor oil, glyceryl palmitostearate, glyceryl behenate, cetyl alcohol, polyvinylpyrrolidone, glycerin, ethylcellulose, methylcellulose, sodium carboxymethylcellulose, as well as other natural or synthetic substances well known to those skilled in the pharmaceutical art, i.e. magnesium stearate, stearic acid, talc, sodium benzoate, boric acid, polyoxyethylene glycols, and colloidal silica.

As will be illustrated in more detail in the examples reported hereinafter, also diluents, binders, lubricants, buffers, antistick and gliding agents, and other substances capable of bringing about the desired characteristics in said layer may be used.

Plasticizing agents are selected from ths group consisting of hydrogenated castor oil, fatty acids, substituted triglycerides and glycerides, polyoxyethylene glycols and derivatives thereof with a different molecular weight generally in the range 400 to 60,000.

They serve the function of making the intermediate layer as elastic as required and of improving the compressibility, adhesion, and cohesion properties of same.

Said adjuvants, in combination with the polymeric materials mentioned above, can better define the barrier function time, which may vary from 15 min to more than 6 to 8 hrs depending on the therapeutic requirements.

As mentioned above and as will be illustrated in more detail in the examples reported hereinafter, said barrier-type layer may consists of prevailingly erodible and/or soluble polymers by contact with water and aqueous fluids. Moreover, as a rule, said type of barrier does not significantly affect the rate and kinetics of release of the active ingredient contained in the lower layer.

Conversely, should a therapeutic treatment require that a slow and sustained drug release from the lower layer take place a given time after drug release from the upper layer, said barrier-type layer will preferably consist of gelable polymers. The resulting system will be capable of fast releasing the drug from the upper layer and, after a predetermined time, of releasing the drug from the lower layer gradually and at an in-vitro scheduled rate, which allows maintaining an effective plasmatic level of the drug.

Said intermediate layer is 0.1 to 4.5 mm thick.

Said lower layer may have the same composition as the upper layer and contain an identical or a different active ingredient or a mixture of active ingredients to be released a determined time after release of said active ingredient/s from the upper layer.

Said lower layer is 0.5 to 5 mm thick.

A characteristic of the present invention is that the three-layer tablet is entirely coated (in revolving pan, in fluidized bed or by other procedures) with a polymeric film impermeable to water and aqueous fluids, at least for the time allowing the release both of the first and of the second drug doses. Said impermeable polymeric material is either insoluble or exhibits a delayed solubility or a solubility depending on the pH of the medium.

The film-forming agents that may be used are, e.g., water insoluble polymers, such as ethylcellulose, acrylic resins, i.e. polymers and copolymers of acrylic and methacrylic acids, cellulose acetate propionate; polymers whose solubility depends on the pH of the medium, such as cellulose acetate phthalate, cellulose trimellitate, cellulose acetate butyrate, copolymer of acrylic and methacrylic acids.

The polymeric coating, in respect of the finished tablet total weight, amounts to 0.2 to 20% by wt.

For tablet finishing, the coating layer is partially removed by automated industrial procedures, so as to provide contact between the upper layer containing the first medicament with the dissolution medium in vitro or with biological fluids in vivo.

The removed portion is the raised top above the tablet upper layer. Said removal may be carried out by apparatus and techniques already available on the market and based on automated industrial procedures.

For example, tablets are fed to a vibrating-distributing system suitably adjusted so as to allow an identical positioning of said tablets with raised tops upwards and distribute same on a linear or circular conveying system taking them under an abrading system which scrapes out said raised tops.

Tablets positioning, distribution and transport system may be selected among the systems available on the market and utilized in the pharmaceutical as well as in other industrial sectors, provided with a wide range of equipment.

Abrasion may be carried out by means of a branding/stamping machine for tablets and/or pills, type Markem 280A, but with the inking system replaced by a grinding wheels system, which removes, with a mechanically controllable precision, only the raised top of the coated tablet.

Figure 2:
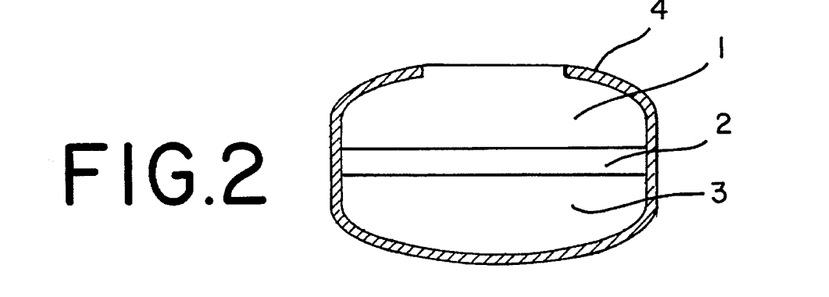
FIG. 2 is a side elevation view of the tablet of FIG. 1 after removal of the raised top.

The tablets so obtained are entirely coated, with the only exception of the area corresponding to the removed raised top FIG. 2). This means that the whole tablet surface, excepting the abraded surface, is impermeable to aqueous fluids.

Should abrasion result in unacceptable aesthetic characteristics (irregularly abraded or rough surface), finished tablets will be further filmed according to traditional techniques, to obtain a polymeric coating, easily soluble and/or dispersible in water and in aqueous fluids, which does not modify the release properties of the finished system in the least.

As set forth in the examples conveyed to further illustrate the present invention, the claimed pharmaceutical tablet for oral administration can release a dose of active ingredient immediately after coming into contact with water or gastric or intestinal fluids and a second dose thereof at a later time depending on the characteristics of the barrier-type layer.

The active ingredients that may be employed in said embodiment are all drugs exerting a therapeutic or protective action against morbid manifestations connected with temporal and, in particular, circadian rhythms, i.e. steroid and non-steroid anti-inflammatory drugs (NSAID), such as diclofenac sodium, indomethacin, ibuprofen, ketoprofen, diflunisal, piroxicam, naproxen, flurbiprofen, tolmetin sodium; antibiotics such as ampicillin, amoxycillin, cephradine, clavulanic acid, cephachlor, cephalexin, cloxacillin, erythromycin, their salts and derivatives; urogenital antimicrobial agents, such as nitrofurantoin, nalidixic acid, oxolinic acid, pipemidic acid and derivatives thereof; sleep producing drugs and tranquillizers, such as diazepam, nitrazepam, flurazepam, oxazepam, chlordiazepoxide, medazepam, lorazepam; drugs for the prevention of anginal and hypertensive attacks, such as diltiazem, trapidil, urapidil, benziodarone, dipiridamole, lidoflazine, naphthydrofuryl oxalate, perhexeline maleate, oxyfedrine hydrochloride; and antihistaminics and/of antiasthmatics, such as ephedrine, terfenadine, theophylline, chlorpheniramine, terbutaline, orciprenaline, aminophylline, isoprenaline, methylpPednisolone, dexamethasone and combinations thereof, ibopanime and salts thereof; drugs for the treatment of ulcers and H2 antagonists, such as cimetidine, famotidine, nizatidine, ranitidine, roxatidine; agents for treating cardiovascular conditions, such as acetobutol, metoprolol, atenolol, nadolol, oxprenolol, bevantolol, bopindol, pindolol, labetalol, propranolol, mepindolol, sotalol; calcium blocking agents, such as nitrendipine, nifedipine, nicardipine, verapamil; ACE inhibitors, such as captopril, enalapril; diuretics, such as hydrochlorothazide, indapamide, piretanide, xipamide; organic nitrates: glyceryl trinitrate, isosorbide dinitrate, isosorbide 5-mononitrate; antiviral drugs, such as aciclovir, AZT.

The compressed tablets of the invention can be prepared from granular mixtures according to current production techniques: therefore, their production on a commercial-scale can be immediate. For example, they can be obtained by rotary presses suitable for producing multi-layer tablets, e.g. Layer-press, Manesty, Liverpool, UK.

The operating pressure usually ranges from 1000 to 5000 kg/cm2. Depending on the procedures adopted, which will be illustrated in more detail in the examples conveyed hereinafter, the three-layer tablets obtained will be spheroid- or ovoid-shaped and in any case without sharp edges, being thus fit for a successive coating by known techniques as illustrated above, e.g. in revolving pan.

EXAMPLE 1

Preparation of a set of 5,000 tablets as per FIG. 2 containing ibopamine hydrochloride as an active ingredient (200 mg each).

1-a-Preparation of the granular mass containing the active ingredient

A granular mass for layers 1 and 3 of FIG. 1 was prepared according to the procedure described hereinafter.

Each layer, which contained 100 mg of active ingredient, had the following composition:

| | |
|---|---|
| Ibopamine hydrochloride | 100.0 mg |
| Maize starch (USP grade, C. Erba, Milan, I) | 100.0 mg |
| Lactose (USP grade, C. Erba, Milan, I) | 20.0 mg |
| Polyvinylpyrrolidone (Plasdone ® K29-32, Gaf Corp., Wayne, NY, USA) | 3.0 mg |
| Anhydrous sodium bicarbonate (C. Erba, Milan, I) | 12.0 mg |
| Anhydrous citric acid (C. Erba, Milan, I) | 10.0 mg |
| Stearic acid (C. Erba, Milan, I) | 5.0 mg |
| Colloidal silica (Syloid 244, Grace GmbH, Worms, D) | 2.0 mg |
| Total | 252.0 mg |

The granular mass was prepared by mixing appropriate quantities of active ingredient, maize starch and lactose in a sigma type mixer, Mod. Erweka, type K5, Frankfurt am Main, D. The mixture was wetted with a 10% w/v alcohol solution of polyvinylpyrrolidone and the uniformly wet mass was forced through a 25 mesh gauze (710 μm) to yield uniformly sized granules. The granular mass was dried in an air circulated oven at 40°–45° C. to constant weight, fed to a mixer for powders (Turbula, Mod. T2A, Bachofen, Basel, CH), added with previously dried sodium bicarbonate, and mixed for 20'. The mixture was then added with citric acid (previously dried), stearic acid and colloidal silica and further mixed for 20 minutes. The granular mass was lubricated, analysed with respect to the active ingredient content, and compressed as described hereinafter.

1-b-Preparation of the granular mass for intermediate barrier-type layer

The quantity of granular mass prepared was as necessary for the production of No. 5000 barrier-type layers, each having the following composition:

| | |
|---|---|
| Hydroxypropyl methylcellulose (Methocel ® E 5 Premium, Colorcon, Orpington, UK) | 88.0 mg |
| Hydrogenated castor oil (Cutina HR, Henkel, Düsseldorf, D) | 19.3 mg |
| Polyvinylpyrrolidone (Plasdone ® K29-32, Gaf Corp., Wayne, NY, USA) | 0.9 mg |
| Green lake (Eingemann-Veronelli, Milan, I) | 0.1 mg |
| Magnesium stearate (USP grade, C. Erba, Milan, I) | 1.1 mg |
| Colloidal silica (Syloid 244, Grace GmbH, Worms, D) | 0.6 mg |
| Total | 110.0 mg |

The granular mass was prepared by mixing appropriate quantities of hydroxypropyl methylcellulose (Methocel E 5: apparent viscosity 5 cps), hydrogenated castor oil and green lake in a sigma type mixer, Mod. Erweka, type K5, Frankfurt am Main, D. The mixture was wetted with a 20% w/v alcohol solution of polyvinylpyrrolidone and the uniformly wet mass was forced through a 25 mesh gauze (710 μm) to yield pale green uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

1-c-Preparation of three-layer tablets

The granular masses obtained as reported in the previous sections and according to schemes well known to those skilled in the apt were loaded into three feed hoppers of a rotary press fit for producing three-layer tablets (e.g. Layer-press, Manesty, Liverpool, UK). In particular, the first and third hoppers were filled with the granular mass as per point 1-a, while the second hopper was filled with the granular mass as per point 1-b.

The press was equipped with circular concave punches (dia. 12 mm and punch bending radius, R, 12 mm). The upper punch had two bending radii (one of 12 mm and the other of 8 mm), which allowed the formation of convex round tablets with a spherical raised top on the upper side (FIG. 1).

The press was set to produce three-layer tablets, one layer consisting of 252 mg of granular mass containing the active ingredient (equalling 100 mg ibopamine hydrochloride), one 110 mg barrier-type layer (this being the quantity necessary to obtain a thickness of approx. 1.0 mm), and one layer consisting of 252 mg of granular mass containing the active ingredient (equalling 100 mg ibopamine hydrochloride).

The three-layer compressed tablets obtained averagely weighed 614 mg and contained two distinct doses of active ingredient (100 mg each).

1-d-Coating by filming

The tablets obtained were filmed in a revolving pan in the presence of a coating solution having the following per cent composition (w/w):

| | |
|---|---|
| Ethylcellulose (Ethocel ® 22 cp, BDH Chem., Poole, UK) | 16.0% |
| Abs. ethanol (C. Erba, Milan, I) | 10.0% |
| Ethyl acetate (C. Erba, Milan, I) | 12.0% |
| Toluene (C. Erba, Milan, I) | 45.0% |
| Butyl acetate (C. Erba, Milan, I) | 13.0% |
| Diethyl phthalate (C. Erba, Milan, I) | 4.0% |

Filming was carried out in a traditional stainless steel basin (dia. 30 cm); the solution of coating polymeric material was sprayed by a traditional air jet system (type Asturo Mec, 1 mm nozzle) or by an airless spraying system (type Graco).

Filming was continued until a 60 mg coating per tablet was applied. Entirely coated three-layer tablets were obtained (FIG. 1).

1-e-Coating partial abrasion

Coated tablets were fed to a vibrating-distributing system positioning said tablets with raised tops upwards and conveying same under an abrading system meant to scrape out the coating from said raised tops.

Positioning and abrasion were carried out by means of a branding machine for tablets and/or pills, type Markem 280A, suitably modified to be provided with a grinding wheels system, which removed, with a mechanically controllable precision, only the coated surface of the raised top of the tablet.

The tablets obtained according to the above procedure were entirely coated with the only exception of the abraded area (FIG. 2). This means that the whole tablet surface, excepting the abraded surface, is impermeable to aqueous fluids.

1-f-Dissolution test

The tablet release characteristics were evaluated by apparatus 2 (paddle) disclosed in USP XXII, operated at 100 rpm. The dissolution fluid was deionized water at 37° C. Drug release was controlled by UV spectrophotometer set at 263 nm, using an automatic sampling and reading system (Spectracomp 602 of Advanced Products, Milan, Italy).

The results obtained are shown in Table 1.

TABLE 1

| Time (min) | Release (%) |
| --- | --- |
| 5 | 13.2 |
| 15 | 40.2 |
| 30 | 48.8 |
| 45 | 50.8 |
| 60 | 51.9 |
| 90 | 53.6 |
| 120 | 81.6 |
| 150 | 99.9 |

The above data provide evidence that the tablets prepared as disclosed in this Example fast release the first drug dose (50% of the total dose contained in the system) within 15 to 30 min, do not release any drug for a 90-min time interval, and fast release the second drug dose approx. 2 hrs after the dissolution test start. Said behaviour fully matches the goals of the present invention.

EXAMPLE 2

Preparation of a set of 5,000 tablets as per FIG. 2 containing ibopamine hydrochloride as an active ingredient, as described in Example 1, but comprising a different barrier-type layer capable of lengthening the time between the successive releases of the first and of the second dose of drug.

2-a-Preparation of the granular mass containing the active ingredient (ibopamine hydrochloride)

The granular mass was prepared as described in Example 1, point 1a.

2-b-Preparation of the granular mass fop intermediate barrier-type layer

The quantity of granular mass prepared was as necessary for the production of No. 5000 barrier-type layers, each having the following composition:

| | |
| --- | --- |
| Hydroxypropyl methylcellulose (Methocel ® E 50 Premium, Colorcon, Orpington, UK) | 88.0 mg |
| Hydrogenated castor oil (Cutina HR, Henkel, Düsseldorf, D) | 19.3 mg |
| Polyvinylpyrrolidone (Plasdone ® K29-32, Gaf Corp., Wayne, NY, USA) | 0.9 mg |
| Orange lake (Eingemann-Veronelli, Milan, I) | 0.1 mg |
| Magnesium stearate (USP grade, C. Erba, Milan, I) | 1.1 mg |

-continued

| | |
| --- | --- |
| Colloidal silica (Syloid 244, Grace GmbH, Worms, D) | 0.6 mg |
| Total | 110.0 mg |

The granular mass was prepared by mixing appropriate quantities of hydroxypropyl methylcellulose (Methocel E 50: apparent viscosity 50 cps), hydrogenated castor oil and orange lake in a sigma type mixer, Mod. Erweka, type K5, Frankfurt am Main, D. The powder mixture was wetted with a 20% w/v alcohol solution of polyvinylpyrrolidone and the wet mass was forced through a 25 mesh gauze (710 µm) to yield pale orange uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

2-c-Preparation of three-layer tablets

It was carried out as described in Example 1, point 1-c. In particular, the first and third feed hoppers of a rotary press (Layer-press, Manesty, Liverpool, UK) were filled with the granular mass as per point 2-a, while the second hopper was filled with the granular mass forming the barrier-type layer, as described under 2-b.

The three-layer tablets so obtained averagely weighed 614 mg and contained two distinct doses of active ingredient (100 mg each).

2-d-Coating by filming

Coating by filming was carried out as described in Example 1, point 1-d.

2-e-Coating partial abrasion

Partial abrasion of the coating was carried out as described in Example 1, point 1-e.

2-f-Dissolution test

Tests were carried out as described in Example 1, point 1-f. The results obtained are shown in Table 2.

TABLE 2

| Time (h) | Release (%) |
| --- | --- |
| 0.5 | 44.2 |
| 2 | 47.0 |
| 5 | 50.5 |
| 6 | 54.9 |
| 7 | 63.7 |
| 8 | 70.0 |
| 10 | 77.9 |
| 12 | 85.5 |
| 14 | 98.8 |

The above data provide evidence that the tablets so prepared fast release the first drug dose (50% of the total dose) within 30 min, do not release any drug for a time interval of approx. 6 to 7 hrs, and release the second drug dose approx. 7 hrs after the dissolution test start.

Said behaviour fully matches the goals of the present invention.

EXAMPLE 3

Preparation of a set of tablets as per FIG. 2 containing ibopamine hydrochloride as an active ingredient.

3-a-Preparation of the granular mass containing the active ingredient

A granular mass for layers 1 and 3 of FIG. 1 was obtained according to the procedure described hereinafter.

Each layer, which contained 100 mg of active ingredient, had the following composition:

| | |
|---|---|
| Ibopamine hydrochloride | 100.0 mg |
| Maize starch (USP grade, C. Erba, Milan, I) | 60.0 mg |
| Polyvinylpyrrolidone (Plasdone ® K29-32, Gaf Corp., Wayne, NY, USA) | 3.0 mg |
| Extragranular maize starch (C. Erba, Milan, I) | 19.0 mg |
| Carboxymethyl starch (Explotab ®, Edward Mendell Co. Inc., Carmel, NY, USA) | 55.0 mg |
| Cross-linked polyvinylpyrrolidone (Plasdone ® XL, Gaf Corp., Wayne, NY, USA) | 19.0 mg |
| Magnesium stearate (C. Erba, Milan, I) | 3.0 mg |
| Total | 259.0 mg |

The granular mass was prepared by mixing appropriate quantities of active ingredient and maize starch in a sigma type mixer, Mod. Erweka, type K5, Frankfurt am Main, D. The powder mixture was wetted with a 10% w/v alcohol solution of polyvinylpyrrolidone and the uniformly wet mass was forced through a 25 mesh gauze (710 μm) to yield uniformly sized granules. The granular mass was dried in an air circulated oven at 40°-45° C. to constant weight, fed to a mixer for powders (Turbula, Mod. T2A, Bachofen, Basel, CH), added with extragranular maize starch, carboxymethyl starch and cross-linked polyvinylpyrrolidone, and mixed for 20'. The mixture was then added with magnesium stearate and further mixed for 20 minutes. The granular mass was lubricated, analysed with respect to the active ingredient content, and compressed as described hereinafter.

3-b-Preparation of the granular mass for intermediate barrier-type layer

The quantity of granular mass prepared was as necessary for the production of No. 5000 barrier-type layers, each having the composition as per Example 1, point 1-b.

The granular mass was lubricated and compressed as described hereinafter.

3-c-Preparation of three-layer tablets

The granular masses obtained as reported in the previous sections and according to schemes well known to those skilled in the art were loaded into three feed hoppers of a rotary press fit for producing three-layer tablets (e.g. Layer-press, Manesty, Liverpool, UK). In particular, the first and third hoppers were filled with the granular mass as per point 3-a, while the second hopper was filled with the granular mass as per point 3-b.

The press was equipped with circular concave punches (dia. 12 mm and punch bending radius, R, 12 mm). The upper punch had two bending radii (one of 12 mm and the other of 8 mm), which allowed the formation of convex round tablets with double convexity on one side. The press was set to produce three-layer tablets, one layer consisting of 259 mg of granular mass containing the active ingredient (equalling 100 mg ibopamine hydrochloride), one 110 mg barrier-type layer (this being the quantity necessary to obtain a thickness of approx. 1.0 mm), and one layer consisting of 259 mg of granular mass containing the active ingredient (equalling 100 mg ibopamine hydrochloride).

The three-layer compressed tablets obtained averagely weighed 628 mg and contained two distinct doses of active ingredient (100 mg each).

3-d-Coating by filming

The tablets obtained were filmed in a revolving pan in the presence of a coating solution having the following percent composition (w/w):

Polymer of methacrylic acid and methacrylic

| | |
|---|---|
| Polymer of methacrylic acid and methacrylic acid methyl ester (Eudragit ® S 100, Rhom Pharma, Darmstadt, D) | 5.0% |
| Castor oil (C. Erba, Milan, I) | 0.5% |
| Acetone (C. Erba, Milan, I) | 34.5% |
| Isopropyl alcohol (C. Erba, Milan, I) | 60.0% |

Filming was carried out in a traditional stainless steel revolving pan (dia. 30 cm); the solution of coating polymeric material was sprayed by a traditional air jet system (type Asturo Mec, 1 mm nozzle) or by an airless spraying system (type Graco).

Filming was continued until a 60 mg coating per tablet was applied. Entirely coated three-layer tablets were obtained (FIG. 1).

3-e-Coating partial abrasion

Partial abrasion of the coating was carried out as described in Example 1, point 1-e.

3-f-Dissolution test

The tablet release characteristics were evaluated by apparatus 2 (paddle) disclosed in USP XXII, operated at 100 rpm. The dissolution fluid was deionized water at 37° C. Drug release was controlled by UV spectrophotometer set at 263 nm, using an automatic sampling and reading system (Spectracomp 602 of Advanced Products, Milan, Italy). The results obtained are shown in Table 3.

TABLE 3

| Time (min) | Release (%) |
|---|---|
| 15 | 21.7 |
| 30 | 41.9 |
| 60 | 48.3 |
| 90 | 50.4 |
| 120 | 51.7 |
| 150 | 52.9 |
| 180 | 54.8 |
| 240 | 73.0 |
| 300 | 87.7 |
| 360 | 95.0 |
| 420 | 99.7 |
| 480 | 100.2 |

The above data provide evidence that the tablets so prepared fast release the first drug dose (50% of the total dose contained in the system) within 30 to 60 min, do not release any drug for a 150 to 180 minutes' time interval, and fast release the second drug dose 3 to 4 hrs approx. after the dissolution test start. Said behaviour fully matches the goals of the present invention.

EXAMPLE 4

Preparation of a set of 5,000 tablets as per FIG. 2 containing ibopamine hydrochloride as an active ingredient, as described in Example 3, but comprising a different barrier-type layer capable of shortening the time between the successive releases of the first and of the second dose of drug.

4-a-Preparation of the granular mass containing the active ingredient (ibopamine hydrochloride)

The granular mass was prepared as described in Example 3, point 3-a.

4-b-Preparation of the granular mass for intermediate barrier-type layer

The quantity of granular mass prepared was as necessary for the production of No. 5000 barrier-type layers, each having the following composition:

| | |
|---|---|
| Hydroxypropyl methylcellulose (Methocel® E 3 Premium, Colorcon, Orpington, UK) | 84.15 mg |
| Hydrogenated castor oil (Cutina HR, Henkel, Düsseldorf, D) | 20.90 mg |
| Polyvinylpyrrolidone (Plasdone® K29-32, Gaf Corp., Wayne, NY, USA) | 3.19 mg |
| Yellow lake (Eingemann-Veronelli, Milan, I) | 0.11 mg |
| Magnesium stearate (USP grade, C. Erba, Milan, I) | 1.10 mg |
| Colloidal silica (Syloid 244, Grace GmbH, Worms, D) | 0.55 mg |
| Total | 110.0 mg |

The granular mass was prepared by mixing appropriate quantities of hydroxypropyl methylcellulose (Methocel E 3: apparent viscosity 3 cps), hydrogenated castor oil and yellow lake in a sigma type mixer, Mod. Erweka, type K5, Frankfurt am Main, D. The homogeneous powder mixture was wetted with a 20% w/v alcohol solution of polyvinylpyrrolidone and the uniformly wet mass was forced through a 25 mesh gauze (710 μm) to yield pale yellow uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

4-c-Preparation of three-layer tablets

It was carried out as described in Example 3, point 3-c.

In particular, the first and third feed hoppers of a rotary press (Layer-press, Manesty, Liverpool, UK) were filled with the granular mass as per point 4-a, while the second hopper was filled with the granular mass forming the barrier-type layer, as described under 4-b.

The three-layer tablets so obtained averagely weighed 628 mg and contained two distinct doses of active ingredient (100 mg each).

4-d-Coating by filming

Coating by filming was carried out as described in Example 3, point 3-d.

4-e-Coating partial abrasion

Partial abrasion of the coating was carried out as described in Example 1, point 1-e.

4-f-Dissolution test

The tablet release characteristics were evaluated by apparatus 2 (paddle) disclosed in USP XXII, operated at 100 rpm. The dissolution fluid was deionized water at 37° C. Drug release was controlled by UV spectrophotometer set at 263 nm, using an automatic sampling and reading system (Spectracomp 602 of Advanced Products, Milan, Italy). The results obtained are shown in Table 4.

TABLE 4

| Time (min) | Release (%) |
|---|---|
| 30 | 38.6 |
| 60 | 47.0 |
| 90 | 51.1 |
| 120 | 72.8 |
| 150 | 87.0 |
| 180 | 90.9 |
| 240 | 97.0 |
| 300 | 100.1 |

The above data provide evidence that the tablets so prepared fast release the first drug dose (50% of the total dose contained in the system) within 30 to 60 min, do not release any drug for a 30-min time interval, and fast release the second drug dose 90 min approx. after the dissolution test start.

Said behaviour fully matches the goals of the present invention.

EXAMPLE 5

Preparation of a set of 5,000 tablets as per FIG. 2 containing ketoprofen as an active ingredient (2 doses of 50 mg each).

5-a-Preparation of the granular mass containing the active ingredient

A granular mass for layers 1 and 3 of FIG. 1 was obtained according to the procedure described hereinafter.

Each layer, which contained 100 mg of active ingredient, had the following composition:

| | |
|---|---|
| Ketoprofen (Soc. Medicinali, Scandicci, FI, I) | 50.0 mg |
| Maize starch (USP grade, C. Erba, Milan, I) | 40.0 mg |
| Methylcellulose (500 cP, BDH Chem., Poole, UK) | 0.4 mg |
| Cross-linked polyvinylpyrrolidone (Plasdone® XL, Gaf Corp., Wayne, NY, USA) | 10.0 mg |
| Carboxymethyl starch (Explotab®, Edward Mendell Co. Inc., Carmel, NY, USA) | 9.3 mg |
| Magnesium stearate (C. Erba, Milan, I) | 0.5 mg |
| Colloidal silica (Syloid 244, Grace GmbH, Worms, D) | 0.3 mg |
| Total | 110.5 mg |

The granular mass was prepared by mixing appropriate quantities of active ingredient and maize starch in a sigma type mixer, Mod. Erweka, type K5, Frankfurt am Main, D. The powder mixture was wetted with a 1% w/v methylcellulose aqueous solution and the wet mass was forced through a 25 mesh gauze (710 μm) to yield uniformly sized granules. The granular mass was dried in an air circulated oven at 40°–45° C. to constant weight, fed to a mixer for powders (Turbula, Mod. T2A, Bachofen, Basel, CH), added with cross-linked polyvinylpyrrolidone, carboxymethyl starch, and mixed for 20'. The mixture was then added with magnesium stearate and colloidal silica, and further mixed for 20 minutes. The granular mass was lubricated, analysed with respect to the active ingredient content, and compressed as described hereinafter.

5-b-Preparation of the granular mass for intermediate barrier-type layer

The quantity of granular mass prepared was as necessary for the production of No. 5000 barrier-type layers, each weighing 75 mg and having the following composition:

| | |
|---|---|
| Hydroxypropyl methylcellulose (Methocel® E 5 Premium, Colorcon, Orpington, UK) | 60.00 mg |
| Hydrogenated castor oil (Cutina HR, Henkel, Düsseldorf, D) | 13.13 mg |
| Polyvinylpyrrolidone (Plasdone® K29-32, Gaf Corp., Wayne, NY, USA) | 0.67 mg |
| Green lake (Eingemann-Veronelli, Milan, I) | 0.07 mg |
| Magnesium stearate (USP grade, C. Erba, Milan, I) | 0.75 mg |
| Colloidal silica (Syloid 244, Grace GmbH, Worms, D) | 0.38 mg |
| Total | 75.00 mg |

The granular mass was prepared by mixing appropriate quantities of hydroxypropyl methylcellulose (Methocel E 5: apparent viscosity 5 cps), hydrogenated castor oil and green lake in a sigma type mixer, Mod. Erweka, type K5, Frankfurt am Main, D. The homogenous powder mixture was wetted with a 20% w/v alcohol solution of polyvinylpyrrolidone and the uniformly wet mass was forced through a 25 mesh gauze (710 μm) to yield pale green uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

5-c-Preparation of three-layer tablets

The granular masses obtained as reported in the previous sections and according to schemes well known to those skilled in the art were loaded into three feed hoppers of a rotary press fit for producing three-layer tablets (e.g. Layerpress, Manesty, Liverpool, UK). In particular, the first and third hoppers were filled with the granular mass as per point 5-a, while the second hopper was filled with the granular mass as per point 5-b.

The press was equipped with circular concave punches (dia. 10 mm and punch bending radius, R, 10 mm). The upper punch had two bending radii (one of 10 mm and the other of 8 mm), which allowed the formation of convex round tablets with a spherical raised top on the upper side (FIG. 1).

The press was set to produce three-layer tablets, one layer consisting of 110.5 mg of granular mass containing the active ingredient (equalling 50 mg ketoprofen), one 75 mg barrier-type layer (this being the quantity necessary to obtain a thickness of 1.1 mm), and one layer consisting of 110.5 mg of granular mass containing the active ingredient (equalling 50 mg ketoprofen). The three-layer compressed tablets so obtained having diameter of 100 mm averagely weighed 296 mg and contained two distinct doses of active ingredient (50 mg ketoprofen each).

5-d-Coating by filming

The tablets obtained were filmed in a revolving pan in the presence of a coating solution having the following percent composition (w/w):

| Ethylcellulose (Ethocel ® 22 cp, BDH Chem., Poole, UK) | 5.0% |
|---|---|
| Abs. ethanol (C. Erba, Milan, I) | 15.0% |
| Chloroform (C. Erba, Milan, I) | 79.0% |
| Diethylphthalate (C. Erba, Milan, I) | 1.0% |

Filming was carried out in a traditional stainless steel revolving pan (dia. 30 cm); the solution of coating polymeric material was sprayed by a traditional air jet system (type Asturo Mec, 1 mm nozzle) or by an airless spraying system (type Graco).

Filming was continued until a 40 mg coating per tablet was applied. Entirely coated three-layer tablets were obtained (FIG. 1).

5-e-Coating partial abrasion

Coated tablets were fed to a vibrating-distributing system positioning said tablets with raised tops upwards and conveying same under an abrading system meant to scrape out the coating from said raised tops.

Positioning and abrasion were carried out by means of a branding machine for tablets and/or pills, type Markem 280A, suitably modified to be provided with a grinding wheels system, which removed, with a mechanically controllable precision, only the coated surface of the raised top of the tablet.

The tablets obtained according to the above procedure were entirely coated with the only exception of the abraded area (FIG. 2). This means that the whole tablet surface, excepting the abraded surface, is impermeable to aqueous fluids.

5-f-Dissolution test

The tablet release characteristics were evaluated by apparatus 2 (paddle) disclosed in USP XXII, operated at 100 rpm. The dissolution fluid was simulated intestinal fluid, pH 7.5, as per USP XXII, without enzymes, at 37° C. Drug release was controlled by UV spectrophotometer set at 262 nm, using an automatic sampling and reading system (Spectracomp 602 of Advanced Products, Milan, Italy). The results obtained are shown in Table 5.

TABLE 5

| Time (min) | Release (%) |
|---|---|
| 15 | 41.4 |
| 30 | 48.9 |
| 60 | 51.0 |
| 120 | 51.9 |
| 180 | 52.2 |
| 240 | 52.7 |
| 270 | 58.7 |
| 300 | 80.2 |
| 360 | 95.7 |
| 420 | 99.8 |

The above data provide evidence that the tablets so prepared fast release the first drug dose (50% of the total dose) within 30 min, do not release any drug for a time interval of approx. 4 hrs, and fast release the second drug dose approx. 4 hrs and 30 min after the dissolution test start.

Said behaviour fully matches the goals of the present invention.

EXAMPLE 6

Preparation of a set of 5000 tablets as per FIG. 2 containing ketoprofen as an active ingredient (2 doses of 100 mg each).

6-a-Preparation of the granular mass containing the active ingredient

A granular mass containing two doses of active ingredient (100 mg each) to be used for the formation of layers 1 and 3 of FIG. 1 was obtained according to the procedure described in Example 5.

Each layer, which contained 100 mg of ketoprofen, had the following composition:

| Ketoprofen (Soc. Medicinali, Scandicci, FI, I) | 100.0 mg |
|---|---|
| Maize starch (USP grade, C. Erba, Milan, I) | 80.0 mg |
| Methylcellulose (BDH Chem., Poole, UK) | 0.8 mg |
| Cross-linked polyvinylpyrrolidone (Plasdone ® XL, Gaf Corp., Wayne, NY, USA) | 20.0 mg |
| Carboxymethyl starch (Explotab ®, Edward Mendell Co. Inc., Carmel, NY, USA) | 18.6 mg |
| Magnesium stearate (C. Erba, Milan, I) | 1.0 mg |
| Colloidal silica (Syloid 244, Grace GmbH, Worms, D) | 0.6 mg |
| Total | 221.0 mg |

The granular mass was prepared as described in Example 5, point 5-a.

6-b-Preparation of the granular mass for barrier-type layer

The granular mass forming the barrier-type layer was prepared as described in Example 5, point 5-b.

The quantity of granular mass prepared was as necessary for the production of No. 5000 barrier-type layers, each weighing 50 mg and having the following composition:

Hydroxypropyl methylcellulose (Methocel® E 5 Premium,

| | |
|---|---|
| Hydroxypropyl methylcellulose (Methocel ® E 5 Premium, Colorcon, Orpington, UK) | 40.00 mg |
| Hydrogenated castor oil (Cutina HR, Henkel, Düsseldorf, D) | 8.75 mg |
| Polyvinylpyrrolidone (Plasdone ® K29-32, Gaf Corp., Wayne, NY, USA) | 0.45 mg |
| Green lake (Eingemann-Veronelli, Milan, I) | 0.05 mg |
| Magnesium stearate (USP grade, C. Erba, Milan, I) | 0.50 mg |
| Colloidal silica (Syloid 244, Grace GmbH, Worms, D) | 0.25 mg |
| Total | 50.00 mg |

6-c-Preparation of three-layer tablets

It was carried out as described in Example 5, point 5-c.

In particular, the first and third feed hoppers of a rotary press (Layer-press, Manesty, Liverpool, UK) were filled with the granular mass as per point 6-a, while the second hopper was filled with the granular mass forming the barrier-type layer, as described under 6-b.

The press was set to produce three-layer tablets, one layer consisting of 221 mg of granular mass containing the active ingredient (equalling 100 mg ketoprofen), one 50 mg barrier-type layer (this being the quantity necessary to obtain a thickness of 0.8 mm), and one layer consisting of 221 mg of granular mass containing the active ingredient (equalling 100 mg ketoprofen).

The three-layer compressed tablets so obtained having a diameter of 10 mm averagely weighed 492 mg and contained two distinct doses of active ingredient (100 mg each).

6-d-Coating by filming

The tablets obtained were filmed in a revolving pan as described in Example 5, point 5-d. Filming was continued until a 50 mg coating per tablet was applied.

6-e-Coating partial abrasion

Partial abrasion of the coating was carried out as described in Example 1, point 1-e.

6-f-Dissolution test

The tablet release characteristics were evaluated by the apparatus and according to the procedure described in Example 5, point 5-e. The results obtained are shown in Table 6.

TABLE 6

| Time (min) | Release (%) |
|---|---|
| 15 | 33.0 |
| 30 | 44.5 |
| 60 | 50.7 |
| 90 | 51.7 |
| 120 | 52.0 |
| 180 | 52.3 |
| 240 | 85.7 |
| 270 | 100.1 |
| 300 | 100.2 |

The above data provide evidence that the tablets prepared with the same formulation as per Example 5, but containing double the amount of active ingredient (two 100 mg doses of ketoprofen) and comprising a thinner barrier-type layer, release the drug in two distinct pulses within a shorter time interval, i.e. after 3 hrs instead of 4 hrs. Therefore, the function of the barrier-type layer of controlling the time interval between the two release pulses was proved.

EXAMPLE 7

Preparation of a set of 5,000 tablets as per FIG. 2 containing diclofenac sodium as an active ingredient (2 doses of 75 mg each).

7-a-Preparation of the granular mass containing the active ingredient

A granular mass for layers 1 and 3 of FIG. 1 was obtained according to the procedure described hereinafter.

Each layer, which contained 75 mg of active ingredient, had the following composition:

| | |
|---|---|
| Diclofenac sodium (Secifarma, Milan, I) | 75.0 mg |
| Maize starch (USP grade, C. Erba, Milan, I) | 100.0 mg |
| Lactose (C. Erba, Milan, I) | 90.0 mg |
| Polyvinylpyrrolidone (Plasdone ® K29-32, Gaf Corp., Wayne, NY, USA) | 6.0 mg |
| Anhydrous sodium bicarbonate (C. Erba, Milan, I) | 12.0 mg |
| Anhydrous citric acid (C. Erba, Milan, I) | 10.0 mg |
| Stearic acid (C. Erba, Milan, I) | 5.0 mg |
| Colloidal silica (Syloid 244, Grace GmbH, Worms, D) | 2.0 mg |
| Total | 300.0 mg |

The granular mass was prepared by mixing appropriate quantities of active ingredient, maize starch and lactose in a sigma type mixer, Mod. Erweka, type K5, Frankfurt am Main, D. The powder mixture was wetted with a 10% w/v alcohol solution of polyvinylpyrrolidone and the wet mass was forced through a 25 mesh gauze (710 µm) to yield uniformly sized granules. Said granular mass was dried in an air circulated oven at 40°–45° C. to constant weight, fed to a mixer for powders (Turbula, Mod. T2A, Bachofen, Basel, CH), added with previously dried sodium bicarbonate, and mixed for 20'. The mixture was then added with citric acid (previously dried), stearic acid, and colloidal silica, and further mixed for 20 minutes. The granular mass was lubricated, analysed with respect to the active ingredient content, and compressed as described hereinafter.

7-b-Preparation of the granular mass for intermediate barrier-type layer

The quantity of granular mass prepared was as necessary for the production of No. 5000 barrier-type layers, each having the following composition:

| | |
|---|---|
| Hydroxypropyl methylcellulose (Methocel ® E 5 Premium, Colorcon, Orpington, UK) | 100.00 mg |
| Hydrogenated castor oil (Cutina HR, Henkel, Düsseldorf, D) | 21.88 mg |
| Polyvinylpyrrolidone (Plasdone ® K29-32, Gaf Corp., Wayne, NY, USA) | 1.12 mg |
| Green lake (Eingemann-Veronelli, Milan, I) | 0.12 mg |
| Magnesium stearate (USP grade, C. Erba, Milan, I) | 1.26 mg |
| Colloidal silica (Syloid 244, Grace GmbH, Worms, D) | 0.62 mg |
| Total | 125.00 mg |

The granular mass was prepared by mixing appropriate quantities of hydroxypropyl methylcellulose (Methocel E 5: apparent viscosity 5 cps), hydrogenated castor oil and green lake in a sigma type mixer, Mod. Erweka, type K5, Frankfurt am Main, D. The homogeneous powder mixture was wetted with a 20% w/v alcohol solution of polyvinylpyrrolidone and the wet mass was forced through a 25 mesh gauze (710 µm) to yield pale green uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

7-c-Preparation of three-layer tablets

The granular masses obtained as reported in the previous sections and according to schemes well known to those skilled in the art were loaded into three feed hoppers of a rotary press fit for producing three-layer tablets (e.g. Layer-press, Manesty, Liverpool, UK). In particular, the first and third hoppers were filled with the granular mass as per point 7-a, while the second hopper was filled with the granular mass as per point 7-b.

The press was equipped with circular concave punches (dia. 12 mm and punch bending radius, R, 12 mm). The upper punch had two bending radii (one of 12 mm and the other of 8 mm), which allowed the formation of convex round tablets with a spherical raised top on one side (FIG. 1).

The press was set to produce three-layer tablets, one layer consisting of 300 mg of granular mass containing the active ingredient (equalling 75 mg diclofenac sodium), one 125 mg barrier-type layer (this being the quantity necessary to obtain a thickness of 1.1 mm), and one layer consisting of 300 mg of granular mass containing the active ingredient (equalling 75 mg diclofenac sodium).

The three-layer compressed tablets so obtained averagely weighed 725 mg and contained two distinct doses of active ingredient (75 mg each).

7-d-Coating by filming

The tablets obtained were filmed in a revolving pan in the presence of a coating solution having the following per cent composition (w/w):

| | |
|---|---|
| Polymer of methacrylic acid and methacrylic acid methyl ester (Eudragit ® S 100, Rhom Pharma, Darmstadt, D) | 5.0% |
| Castor oil (C. Erba, Milan, I) | 0.5% |
| Acetone (C. Erba, Milan, I) | 34.5% |
| Isopropyl alcohol (C. Erba, Milan, I) | 60.0% |

Filming was carried out in a traditional stainless steel revolving pan (dia. 30 cm); the solution of coating polymeric material was sprayed by a traditional air jet system (type Asturo Mec, 1 mm nozzle).

Filming was continued until a 60 mg coating per tablet was applied. Entirely coated three-layer tablets were obtained (FIG. 1).

7-e-Coating partial abrasion

Partial abrasion of the coating was carried out as described in Example 1, point 1-e.

7-f-Dissolution test

The tablet release characteristics were evaluated by apparatus 2 (paddle) disclosed in USP XXII, operated at 100 rpm. The dissolution fluid was deionized water at 37° C. Drug release was controlled by UV spectrophotometer set at 276 nm, using an automatic sampling and reading system (Spectracomp 602 of Advanced Products, Milan, Italy). The results obtained are shown in Table 7.

TABLE 7

| Time (min) | Release (%) |
|---|---|
| 15 | 29.5 |
| 30 | 45.3 |
| 60 | 50.2 |
| 120 | 51.5 |
| 180 | 58.4 |

TABLE 7-continued

| Time (min) | Release (%) |
|---|---|
| 240 | 98.4 |
| 300 | 101.5 |

The above data provide evidence that the tablets so prepared fast release the first drug dose (50% of the total dose contained in the system) within 30 min, do not release any drug for a 150-min time interval, and fast release the second drug dose approx. 3 hrs after the dissolution test start.

Said behaviour fully matches the goals of the present invention.

EXAMPLE 8

Preparation of a set of 5,000 tablets as per FIG. 2 containing diclofenac sodium as an active ingredient, as described in Example 7, but comprising a different barrier-type layer capable of lengthening the time between the successive releases of the first and of the second dose of drug.

8-a-Preparation of the granular mass containing the active ingredient (diclofenac sodium)

The granular mass was prepared as described in Example 7, point 7-a.

8-b-Preparation of the granular mass for intermediate barrier-type layer

The quantity of granular mass prepared was as necessary for the production of No. 5000 barrier-type layers, each having the following composition:

| | |
|---|---|
| Hydroxypropyl methylcellulose (Methocel ® E 50 Premium, Colorcon, Orpington, UK) | 100.00 mg |
| Hydrogenated castor oil (Cutina HR, Henkel, Düsseldorf, D) | 21.88 mg |
| Polyvinylpyrrolidone (Plasdone ® K29-32, Gaf Corp., Wayne, NY, USA) | 1.12 mg |
| Orange lake (Eingemann-Veronelli, Milan, I) | 0.12 mg |
| Magnesium stearate (USP grade, C. Erba, Milan, I) | 1.26 mg |
| Colloidal silica (Syloid 244, Grace GmbH, Worms, D) | 0.62 mg |
| Total | 125.00 mg |

The granular mass was prepared by mixing appropriate quantities of hydroxypropyl methylcellulose (Methocel E 50: apparent viscosity 50 cps), hydrogenated castor oil and orange lake in a sigma type mixer, Mod. Erweka, type K5, Frankfurt am Main, D. The homogeneous powder mixture was wetted with a 20% w/v alcohol solution of polyvinylpyrrolidone and the uniformly wet mass was forced through a 25 mesh gauze (710 μm) to yield pale orange uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

8-c-Preparation of three-layer tablets (by compression)

It was carried out as described in Example 7, point 7-c.

In particular, the first and third feed hoppers of a rotary press (Layer-press, Manesty, Liverpool, UK) were filled with the granular mass as per point 7-a, while the second hopper was filled with the granular mass as described under 7-b.

The three-layer tablets so obtained averagely weighed 725 mg and contained two distinct doses of active ingredient (75 mg each).

8-d-Coating by filming

Coating by filming was carried out as described in Example 7, point 7-d.

8-e-Coating partial abrasion

Partial abrasion of the coating was carried out as described in Example 1, point 1-e.

8-f-Dissolution test

The tablet release characteristics were evaluated by the apparatus and according to the procedure described in Example 7, point 7-e. The results obtained are shown in Table 8.

TABLE 8

| Time (h) | Release (%) |
|---|---|
| 0.5 | 47.0 |
| 1 | 49.6 |
| 2 | 51.7 |
| 3 | 52.8 |
| 4 | 53.4 |
| 5 | 53.9 |
| 6 | 54.4 |
| 7 | 57.2 |
| 8 | 90.2 |
| 9 | 98.9 |
| 10 | 99.8 |

The above data provide evidence that the tablets so prepared fast release the first drug dose (50% of the total dose contained in the system) within apppox. 30 min, do not release any drug fop a time interval of approx. 6 hrs, and release the second drug dose approx. 7 to 8 hrs after the dissolution test start.

Said behaviour fully matches the goals of the present invention.

EXAMPLE 9

Preparation of a set of 5,000 tablets as per FIG. 2 containing ibuprofen as an active ingredient (2 doses of 200 mg each).

9-a-Preparation of the granular mass containing the active ingredient

A granular mass for layers 1 and 3 of FIG. 1 was obtained according to the procedure described hereinafter.

Each layer, which contained 200 mg of active ingredient, had the following composition:

| | |
|---|---|
| Ibuprofen (Francis, Milan, I) | 200.0 mg |
| Maize starch (C. Erba, Milan, I) | 59.7 mg |
| Methylcellulose (500–600 cP, BDH, Poole, UK) | 1.0 mg |
| Sodium lauryl sulphate (C. Erba, Milan, I) | 0.7 mg |
| Cross-linked polyvinylpyrrolidone (Plasdone ® XL, Gaf Corp., Wayne, NY, USA) | 6.0 mg |
| Cross-linked sodium starch glycolate (Primojel ®, Avebe, Foxhol, NL) | 15.0 mg |
| Magnesium stearate (C. Erba, Milan, I) | 2.6 mg |
| Total | 285.0 mg |

The granular mass was prepared by mixing appropriate quantities of active ingredient and half amount of maize starch in a sigma type mixer, Mod. Erweka, type K5, Frankfurt am Main, D. The powder mixture was wetted with sodium lauryl sulphate dissolved in a 1% w/v aqueous solution of methylcellulose and the wet mass was forced through a 25 mesh gauze (710 µm) to yield uniformly sized granules. The granular mass was dried in an air circulated oven at 40°–45° C. to constant weight, fed to a mixer for powders (Turbula, Mod. T2A, Bachofen, Basel, CH), added with magnesium stearate and mixed for 20'. The mixture was then added with cross-linked polyvinylpyrrolidone, the remaining half of maize starch and cross-linked sodium starch glycolate, and further mixed for 20 minutes. The granular mass was analysed with respect to the active ingredient content and compressed as described hereinafter.

9-b-Preparation of the granular mass for intermediate barrier-type layer

The quantity of granular mass prepared was as necessary for the production of No. 5000 barrier-type layers, each having the following composition:

| | |
|---|---|
| Hydroxypropyl methylcellulose (Methocel ® E 3 Premium, Colorcon, Orpington, UK) | 76.5 mg |
| Hydrogenated castor oil (Cutina HR, Henkel, Düsseldorf, D) | 19.0 mg |
| Polyvinylpyrrolidone (Plasdone ® K29-32, Gaf Corp., Wayne, NY, USA) | 2.9 mg |
| Yellow lake (Eingemann-Veronelli, Milan, I) | 0.1 mg |
| Magnesium stearate (USP grade, C. Erba, Milan, I) | 1.0 mg |
| Colloidal silica (Syloid 244, Grace GmbH, Worms, D) | 0.5 mg |
| Total | 100.0 mg |

The granular mass was prepared by mixing appropriate quantities of hydroxypropyl methylcellulose (Methocel E 3: apparent viscosity 3 cps), hydrogenated castor oil and yellow lake in a sigma type mixer, Mod. Erweka, type K5, Frankfurt am Main, D. The powder mixture was wetted with a 10% w/v alcohol solution of polyvinylpyrrolidone and the wet mass was forced through a 25 mesh gauze (710 µm) to yield pale yellow uniformly sized granules. The granular mass was dried in an air circulated oven at 40°–45° C. to constant weight, fed to a mixer for powders (Turbula, Mod. T2A), added with magnesium stearate and colloidal silica and mixed for 20'. The granular mass was lubricated and compressed as described hereinafter.

9-c-Preparation of three-layer tablets

The granular masses obtained as reported in the previous sections and according to schemes well known to those skilled in the art were loaded into three feed hoppers of a rotary press fit for producing three-layer tablets (e.g. Layer-press, Manesty, Liverpool, UK). In particular, the first and third hoppers were filled with the granular mass as per point 9-a, while the second hopper was filled with the granular mass as per point 9-b.

The press was equipped with circular concave punches (dia. 12 mm and punch bending radius, R, 12 mm). The upper punch had two bending radii (one of 12 mm and the other of 8 mm), which allowed the formation of convex round tablets with a spherical raised top on one side.

The press was set to produce three-layer tablets, one layer consisting of 285 mg of granular mass containing the active ingredient (equalling 200 mg ibuprofen), one 100 mg barrier-type layer (this being the quantity necessary to obtain a thickness of 0.9 mm), and one layer consisting of 285 mg of granular mass containing the active ingredient (equalling 200 mg ibuprofen).

The three-layer compressed tablets so obtained having a diameter of 12 mm averagely weighed 670 mg and contained two distinct doses of active ingredient (200 mg each).

9-d-Coating by filming

The tablets obtained were filmed in a revolving pan in the presence of a coating solution having the following percent composition (w/w):

| | |
|---|---|
| Ethylcellulose (Ethocel ® 22 cp, BDH Chem., Poole, UK) | 5.0% |
| Abs. ethanol (C. Erba, Milan, I) | 15.0% |
| Chloroform (C. Erba, Milan, I) | 79.0% |
| Diethyl phthalate (C. Erba, Milan, I) | 1.0% |

Filming was carried out in a traditional stainless steel revolving pan (dia. 30 cm); the solution of coating polymeric material was sprayed by a traditional air jet system (type Asturo Mec, 1 mm nozzle).

Filming was continued until a 60 mg coating per tablet was applied. Entirely coated three-layer tablets were obtained (FIG. 1).

9-e-Coating partial abrasion

Partial abrasion of the coating was carried out as described in Example 1, point 1-e.

9-f-Dissolution test

The tablet release characteristics were evaluated by apparatus 2 (paddle) disclosed in USP XXII, operated at 100 rpm. The dissolution fluid was simulated intestinal fluid, pH 7.5, as per USP XXII, without enzymes, at 37° C. Drug release was controlled by UV spectrophotometer set at 223 nm, using an automatic sampling and reading system (Spectracomp 602 of Advanced Products, Milan, Italy). The results obtained are shown in Table 9.

TABLE 9

| Time (min) | Release (%) |
|---|---|
| 30 | 37.9 |
| 60 | 51.0 |
| 90 | 49.3 |
| 120 | 50.5 |
| 150 | 51.7 |
| 180 | 59.2 |
| 240 | 78.4 |
| 270 | 83.6 |
| 300 | 88.2 |
| 360 | 94.3 |
| 420 | 98.4 |

The above data provide evidence that the tablets so prepared fast release the first drug dose (50% of the total dose) within approx. 30 min, do not release any drug for a time interval of approx. 2 hrs, and fast release the second drug dose approx. 3 hrs after the dissolution test start.

Said behaviour fully matches the goals of the present invention.

We claim:

1. Process for the preparation of a pharmaceutical tablet containing one or more drugs, capable of releasing said drugs at subsequent times, said tablet comprising upper, intermediate and lower superposed layers, said upper layer comprising a drug which is formulated to provide for the immediate release of said drug upon contact with aqueous fluids; said intermediate layer being formulated without any drug but being formulated to slowly erode or dissolve upon contact with aqueous fluids; and said lower layer comprising a drug which is the same as the drug in said upper layer or which is different from the drug in said upper layer and is also formulated to provide for the immediate release of said drug upon contact with aqueous fluids, said process comprising:

(a) preparing a tablet having said upper, intermediate and lower layers wherein either of said upper or lower layers has an elevated portion of the outer surface which is elevated with respect with the other portion of said outer surface;

(b) coating the surface of the tablet of step (a) with a polymeric film which is impermeable to aqueous fluids;

(c) removing, by abrasion, said elevated portion of the outer surface of either of said upper or lower layers to allow contact of said upper or lower layer with the environment; and (d) coating the tablet obtained in step (c) with a polymeric material which is soluble in aqueous fluids.

2. The process of claim 1 wherein the layer which has the elevated portion is from 0.5 to 5 mm thick and contains 1 to 90% by weight of the drug.

3. The process of claim 1 wherein said intermediate layer is 0.1 to 4.5 mm thick and contains 1 to 90% by weight of a soluble or erodible surface.

4. The process of claim 1 wherein said polymeric film which is impermeable to aqueous fluids consists essentially of a polymer selected from the group consisting of ethylcellulose, acrylic polymers, methacrylic polymers, copolymers of acrylic acid, copolymers of methacrylic acid, cellulose acetoproprionate, cellulose aceto-phthalate and cellulose trimellitate.

5. The process of claim 1 wherein said upper layer has the elevated portion.

6. The process of claim 1 wherein said lower layer has the elevated portion.

7. Process for the preparation of pharmaceutical tablet containing one or more drugs, capable of releasing said drugs at subsequent times, said tablet comprising upper, intermediate and lower superposed layers, said upper layer comprising a drug which is formulated to provide for the immediate release of said drug upon contact with aqueous fluids; said intermediate layer being formulated without any drug but being formulated to slowly erode or dissolve upon contact with aqueous fluids; and said lower layer comprising a drug which is the same as the drug in said upper layer and is also formulated to provide for the immediate release of said drug upon contact with aqueous fluids, said process comprising:

(a) preparing a tablet having said upper, intermediate and lower layers wherein said upper layer has an elevated portion of the outer surface which is elevated with respect with the other portion of said outer surface;

(b) coating the surface of the tablet of step (a) with a polymeric film which is impermeable to aqueous fluids;

(c) removing, by abrasion said elevated portion of the outer surface of said upper layer to allow contact of said upper layer with the environment; and (d) coating the tablet obtained in step (c) with a polymeric material which is soluble in aqueous fluids.

8. The process of claim 7 wherein the layer which has the elevated portion is from 0.5 to 5 mm thick and contains 1 to 90% by weight of the drug.

9. The process of claim 1 wherein the lower layer contains a drug which is different from the drug in said upper layer.

10. The process of claim 1 wherein the lower layer contains a drug which is the same as the drug in said upper layer.

* * * * *